United States Patent
Lacorte et al.

(10) Patent No.: US 12,246,036 B2
(45) Date of Patent: Mar. 11, 2025

(54) COMPOSITION FOR USE IN THE PREVENTION AND IN THE TREATMENT OF IRON DEFICIENCY

(71) Applicant: PHARMANUTRA S.P.A., Pisa (IT)

(72) Inventors: Andrea Lacorte, Pisa (IT); Germano Tarantino, Pisa (IT)

(73) Assignee: PHARMANUTRA S.P.A., Pisa (IT)

( * ) Notice: Subject to any disclaimer, the term of this patent is extended or adjusted under 35 U.S.C. 154(b) by 0 days.

(21) Appl. No.: 16/635,516

(22) PCT Filed: Jul. 27, 2018

(86) PCT No.: PCT/IB2018/055634
§ 371 (c)(1),
(2) Date: Jan. 30, 2020

(87) PCT Pub. No.: WO2019/025922
PCT Pub. Date: Feb. 7, 2019

(65) Prior Publication Data
US 2020/0246377 A1    Aug. 6, 2020

(30) Foreign Application Priority Data
Aug. 2, 2017 (IT) .................... 102017000089258

(51) Int. Cl.
| A61K 33/26 | (2006.01) |
| A23L 33/00 | (2016.01) |
| A23L 33/155 | (2016.01) |
| A23L 33/16 | (2016.01) |
| A61K 9/00 | (2006.01) |

(Continued)

(52) U.S. Cl.
CPC .............. *A61K 33/26* (2013.01); *A23L 33/155* (2016.08); *A23L 33/16* (2016.08); *A23L 33/40* (2016.08); *A61K 9/0053* (2013.01); *A61K 31/593* (2013.01); *A61P 29/00* (2018.01); *A23V 2002/00* (2013.01)

(58) Field of Classification Search
None
See application file for complete search history.

(56) References Cited

U.S. PATENT DOCUMENTS

| 4,113,881 A | 9/1978 | Diehl |
| 4,393,133 A | 7/1983 | Knowles et al. |

(Continued)

FOREIGN PATENT DOCUMENTS

| CN | 106343566 A | * | 1/2017 |
| CN | 108137472 A | | 6/2018 |

(Continued)

OTHER PUBLICATIONS

Muriuki et al., "Malaria is a cause of iron deficiency in African childern", Nature Medicine vol. 27, pp. 653-658 (2021) (see e.g., abstract, pp. 653-654 and 657). (Year: 2021).*

(Continued)

*Primary Examiner* — Kyung S Chang
(74) *Attorney, Agent, or Firm* — Steinfl + Bruno LLP (57) ABSTRACT

The present invention relates to a composition for use in a method for the preventive or curative treatment of an iron deficiency and pathologies and disorders connected thereto in a subject. The disclosed methods include administering the composition to a subject in need thereof.

17 Claims, 2 Drawing Sheets

(51) Int. Cl.
*A61K 31/593* (2006.01)
*A61P 29/00* (2006.01)

(56) References Cited

U.S. PATENT DOCUMENTS

| | | | |
|---|---|---|---|
| 5,888,563 | A | 3/1999 | Mehansho et al. |
| 6,039,978 | A | 3/2000 | Bangs et al. |
| 6,361,800 | B1 | 3/2002 | Cooper et al. |
| 6,417,227 | B1 | 7/2002 | Lord et al. |
| 8,404,745 | B2 | 3/2013 | Barathur et al. |
| 9,861,670 | B2 | 1/2018 | Clements et al. |
| 2002/0058705 | A1 | 5/2002 | Gonzales Bravo et al. |
| 2003/0181521 | A1 | 9/2003 | Leonard et al. |
| 2005/0100636 | A1 | 5/2005 | Botteri et al. |
| 2005/0261257 | A1 | 11/2005 | Vermeer |
| 2007/0065521 | A1* | 3/2007 | Venkataraman ..... A61K 31/555 514/185 |
| 2007/0148258 | A1 | 6/2007 | O'Neill et al. |
| 2007/0148259 | A1 | 6/2007 | Gupta |
| 2009/0186939 | A1 | 7/2009 | Chan et al. |
| 2009/0326060 | A1 | 12/2009 | Chan et al. |
| 2010/0021573 | A1 | 1/2010 | Gonzalez et al. |
| 2011/0054030 | A1 | 3/2011 | Petraglia et al. |
| 2011/0294665 | A1 | 12/2011 | Makino |
| 2012/0265119 | A1 | 10/2012 | Barathur et al. |
| 2013/0157974 | A1 | 6/2013 | Ziegler et al. |
| 2014/0121156 | A1* | 5/2014 | Hausman ............. A61K 31/593 514/5.4 |
| 2014/0322314 | A1 | 10/2014 | Fawzy et al. |
| 2015/0250885 | A1 | 9/2015 | Lacorte et al. |
| 2016/0008415 | A1 | 1/2016 | Clements et al. |
| 2016/0310445 | A1 | 10/2016 | Vermeer |
| 2017/0056465 | A1 | 3/2017 | Tobin et al. |
| 2017/0080023 | A1 | 3/2017 | Agam et al. |
| 2017/0112178 | A1 | 4/2017 | Perrin et al. |
| 2017/0202802 | A1 | 7/2017 | Fernandez et al. |
| 2020/0085710 | A1 | 3/2020 | Denda et al. |
| 2020/0206157 | A1 | 7/2020 | Lacorte et al. |
| 2022/0211655 | A1 | 7/2022 | Lacorte et al. |
| 2022/0220414 | A1 | 7/2022 | Lacorte et al. |
| 2022/0226274 | A1 | 7/2022 | Lacorte et al. |

FOREIGN PATENT DOCUMENTS

| | | |
|---|---|---|
| EP | 0679394 A2 | 11/1995 |
| EP | 2380578 A1 | 10/2011 |
| EP | 2886129 A1 | 6/2015 |
| GB | 2552952 A | 2/2018 |
| JP | S5841813 A | 3/1983 |
| JP | H08253415 A | 10/1996 |
| JP | 2002515866 A | 5/2002 |
| JP | 2003342159 A | 12/2003 |
| JP | 2007523056 A | 8/2007 |
| JP | 2009525277 A | 7/2009 |
| JP | 2015523409 A | 8/2015 |
| NZ | 332959 A | 9/2001 |
| WO | 1997/031620 A2 | 9/1997 |
| WO | 00/64436 A1 | 11/2000 |
| WO | 03/018731 A1 | 3/2003 |
| WO | 2004/019923 A1 | 3/2004 |
| WO | 2004/084829 A2 | 10/2004 |
| WO | 2004/084829 A3 | 1/2005 |
| WO | 2005/044189 A2 | 5/2005 |
| WO | 2007/089577 A2 | 8/2007 |
| WO | 2010/079514 A1 | 7/2010 |
| WO | 2010/117194 A2 | 10/2010 |
| WO | 2012/161572 A1 | 11/2012 |
| WO | 2014/009806 A1 | 1/2014 |
| WO | 2014/160279 A1 | 10/2014 |
| WO | 2016/131993 A2 | 8/2016 |
| WO | 2017/029580 A1 | 2/2017 |
| WO | 2018/034797 A1 | 2/2018 |
| WO | 2018/221534 A1 | 12/2018 |
| WO | 2019/021232 A1 | 1/2019 |
| WO | 2019/025922 A1 | 2/2019 |
| WO | 2020/240438 A1 | 12/2020 |
| WO | 2020/240441 A1 | 12/2020 |
| WO | 2020/240443 A1 | 12/2020 |

OTHER PUBLICATIONS

"Kidney disease" obtained from on-line website: https://en.wikipedia.org/wiki/Kidney_disease, last visit date: May 6, 2021 (Year: 2021).*
Shah et al., "Pharmaceutical characterization and thermodynamic stability assessment of a colloidal iron drug product: Iron sucrose", International Journal of Pharmaceutics 464 (2014) pp. 46-52, (Year: 2014).*
CN106343566A—Google English Translation (Year: 2017).*
U.S. Appl. No. 16/631,426, filed Jan. 15, 2020.
Commission Directive 96/77/EC of Dec. 2, 1996; last amendment M7 Commission Directive 2006/129/EC of Dec. 8, 2006. 165 pages.
Cutcliffe T et al., "Vitamin K2 may reverse calcification of blood vessels in people with kidney disease" *NUTRA Ingredients*, Jun. 2017, 3 pages.
E322-Lechitins: on the web site of INCHEM (Internationally Peer Reviewed Chemical Safety Information), World Health Organization, the following Summary of Evaluations Performed by the Joint FAO/WHO Expert Committee on Food Additives dated Feb. 6, 2004. 1 page. [website: inchem.org/documents/jecfa/jeceval/jec_1261.htm].
Final Office Action for U.S. Appl. No. 16/635,516, filed Jan. 30, 2020 on behalf of Pharmanutra S.P.A. Mail Date: Dec. 1, 2021 15 pages.
Fragala M.S. et al: "Influences of a dietary supplement in combination with an exercise and diet regimen on adipocytokines and adiposity in women who are overweight", European Journal of Applied Physiology, vol. 105, No. 5. 2009, pp. 665-672.
Ilbert, Marianne et al., "Review: Insight into the evolution of the iron oxidation pathways", Biochimica et Biophysica Acta, 1827 (2013), pp. 161-175.
International Preliminary Report on Patentability for International Application No. PCT/IB2018/055586 filed on Jul. 26, 2018 on behalf of Pharmanutra S.P.A. Mail Date: Jan. 28, 2020 7 pages.
International Preliminary Report on Patentability for International Application No. PCT/IB2018/055634 filed on Jul. 27, 2018 on behalf of Pharmanutra S.P.A. Mail Date: Feb. 4, 2020 8 pages.
International Preliminary Report on Patentability for International Application No. PCT/IB2020/055028 filed on May 27, 2020 on behalf of Alesco S.R.L. Mail Date: Nov. 16, 2021 7 pages.
International Preliminary Report on Patentability for International Application No. PCT/IB2020/055031 filed on May 27, 2020 on behalf of Alesco S.R.L. Mail Date: Nov. 16, 2021 9 pages.
International Preliminary Report on Patentability for International Application No. PCT/IB2020/055037 filed on May 27, 2020 on behalf of Alesco S.R.L. Mail Date: Nov. 16, 2021 6 pages.
International Search Report and Written Opinion for International Application No. PCT/IB2018/055586 filed on Jul. 26, 2018 on behalf Pharmanutra S.P.A. Mail Date: Oct. 25, 2018 11 pages.
International Search Report and Written Opinion for International Application No. PCT/IB2018/055634 filed on Jul. 27, 2018 on behalf of Pharmanutra S.P.A. Mail Date: Dec. 4, 2018 12 pages.
International Search Report for International Application No. PCT/IB2020/055028 filed on May 27, 2020 on behalf of Alesco S.R.L. Mail Date: Sep. 9, 2020 4 pages.
International Search Report for International Application No. PCT/IB2020/055031 filed on May 27, 2020 on behalf of Alesco S.R.L. Mail Date: Aug. 28, 2020 5 pages.
International Search Report for International Application No. PCT/IB2020/055037 filed on May 27, 2020 on behalf of Alesco S.R.L. Mail Date: Sep. 10, 2020 4 pages.
Kidney disease—*Wikipedia*, Dated: May 6, 2017, 7 pages.
Muriuki J.M. et al., "Malaria is a cause of iron deficiency in African children" *Nature Medicine*, vol. 27, Apr. 2021, pp. 653-658. 19 pages.
Neven E. et al., "Iron and vascular calcification. Is there a link" *Nephrol Dial Transplant*, 2011, pp. 1137-1145.

(56) References Cited

OTHER PUBLICATIONS

Non-Final Office Action for U.S. Appl. No. 16/631,426, filed Jan. 15, 2020 on behalf of Pharmanutra S.P.A. Mail Date: Nov. 10, 2021 17 pages.
Non-Final Office Action for U.S. Appl. No. 16/635,516, filed Jan. 30, 2020 on behalf of Pharmanutra S.P.A. Mail Date: May 12, 2021 30 pages.
Opinion of the Scientific Panel on Food Additives, Flavourings, Processing Aids and Material in Contact with Food on Sucrose esters of fatty acids, e 473 and sucroglycerides, E 474 based on a request from the Commission related to Sucrose Esters of Fatty Acids (E 473). Question No. EFSA-Q-2003-139. Adopted on Oct. 7, 2004; Modified on Jan. 25, 2006. The EFSA Journal (2004) 106, 1-24.
Restriction Requirement for U.S. Appl. No. 16/631,426, filed Jan. 15, 2020 on behalf of Pharmanutra S.P.A. Mail Date: Aug. 20, 2021 10 pages.
Spiegel D.M. et al., "Long-term effects of magnesium carbonate on coronary artery calcification and bone mineral density in hemodialysis patients: a pilot study" *Hemodial Int.*, Oct. 2009 (Abstract Only) 13(4): 453-9.
Written Opinion for International Application No. PCT/IB2020/055028 filed on May 27, 2020 on behalf of Alesco S.R.L. Mail Date: Sep. 9, 2020 6 pages.
Written Opinion for International Application No. PCT/IB2020/055031 filed on May 27, 2020 on behalf of Alesco S.R.L. Mail Date: Aug. 28, 2020 8 pages.
Written Opinion for International Application No. PCT/IB2020/055037 filed on May 27, 2020 on behalf of Alesco S.R.L. Mail Date: Sep. 10, 2020 5 pages.
Barisani et al. "Iron overload and gene expression in HepG2 cells: analysis by differential display" *FEBS Letters* 2000, 469, 208-212.
"Coordination Complex" from Wikipedia, through the Wayback Machine dated Nov. 18, 2016. 10 pages.
Erni, I. Oswald N. et al. "Chemical characterization of iron (III)-hydroxide-dextrin complexes. A comparative study of commercial preparations with alleged reproductions used in the examination of bioavailability", Arzneimittelforschung, 1984: 34 (11): 1555-9. (Abstract only). 1 page.
Final Office Action for U.S. Appl. No. 16/631,426, filed Jan. 15, 2020 on behalf of Pharmanutra S.P.A. Mail Date: Aug. 11, 2022. 18 Pages.
Garrelds, I. M. et al. "Time dependent production of cytokines and eicosanoids by human monocytic leukaemia U937 cells; effects of glucocorticosteroids" *Mediators Inflamm*, 1999, 8, 229-235.
Huang, Z.B. et al. "HMGB1 release by human liver L02 and HepG2 cells induced by lipopolysaccharide" *Molecular Medicine Reports* 8:103-112, 2013.
"Iron Dextran" from DrugBank, DrugBank Accession No. DB00893, dated Nov. 26, 2022. 14 pages.
"Iron Sucrose" from Wikipedia, through the Wayback Machine dated Oct. 22, 2016. 1 page.
Miki, K. et al. "Extracellular activation of arginase-1 decreases enterocyte inducible nitric oxide synthase activity during systemic inflammation" *Am J Physiol Gastrointest Liver Physiol.* 2009; 297(4): G840-G848.
O'Neill, W.C. et al. "Plasma pyrophosphate and vascular calcification in chronic kidney disease", Nephrol Dial Transplant (2010), 25: 187-191. Doi: 10.1093/ndt/gfp362.
O'Neill, W.C. et al. "Treatment with pyrophosphate inhibits uremic vascular calcification", Kidney Int, Mar. 2011, 76(5): 512-517. 15 pages. Doi: 10.1038/ki.2010.461.
Ozcelik, Berrin. "Fungi/Bactericidal and Static Effect of Ultraviolet Light in 254 and 354 nm wavelengths" *Research Journal of Microbiology* 2007 2 (1): 42-49.
Pepys, M. et al., C-reactive protein: a critical update *J. Clin. Invest.* 2003, 111 (12): 1805-1812.
Rincon, M. "Interleukin-6: from an inflammatory marker to a target for inflammatory diseases" *Trends in Immunology*, Nov. 2012, vol. 33, No. 11, pp. 571-577.
Saliou, C. et al. "Selective inhibition of NF-KB activation by the flavonoid hepatoprotector silymarin in HepG2, Evidence for different activating pathways" *FEBS Letters*, 1998, 440, 8:12.
"Salt (chemistry)" from Wikipedia, through the Wayback Machine dated Feb. 11, 2016. 4 pages.
Shelley, C. S. et al. "During Differentiation of the Monocytic Cell Line U937, PurAlpha Mediates Induction of the CD11c Beta2 Integrin Gene Promoter" *J Immunol*, 2002, 168, 3887-3893.
Smith, E. M.; Tangpricha, V. "Vitamin D and Anemia: Insights into an Emerging Association". Curr Opin Endocrinol Diabetes Obes, 2015, 22(6), 432-438. 14 pages.
Strober W. "Trypan blue exclusion test of cell viability" *Curr Protoc Immunol.* May 2001; Appendix 3: Appendix 3B.
Villarroel P. et al. "Interleukin 6 and lipopolysaccharide modulate hepcidin mRNA expression by HepG2 cells" *Biol Trace Elem Res.* Dec. 2012;150(1-3):496-501.
Zughaier, S.M. et al. "The role of vitamin D in regulating the iron-hepcidin-ferroportin axis in monocytes" *J Clin Transl Endocrinol* (2014) e19-e25.
Barpanda P et al. "Sodium iron pyrophosphate: a novel 3.0V iron-based cathode for sodium-ion batteries", Electrochemistry Communications, vol. 24, Oct. 2012, pp. 116-119.
Breymann, Prof. Dr. Christian. Preventing and Treating Iron Deficiency Anaemia in Pregnant Women. Are we doing our best? Presentation in Zurich, Switzerland, May 15, 2017. 27 pages.
Commission Regulation (EU) No. 231/2012 of Mar. 9, 2012. Specifications for food additives listed on Annexes II and III to Regulation (EC) No. 1333/2008 of the European Parliament and of the Council. Official Journal of the European Union. 295 pages.
The Regulation (EC) No. 1333/2008 of the European Parliament and of the Council of Dec. 16, 2008 on food additives. Dated: Mar. 22, 2023. pp. 346.
"E number" from European Food Safety Authority, Downloaded Jul. 21, 2023. 1 page. Website: www.efsa.europa.eu/en/glossary/e-number#:~:text=A%20number%20used%20in%20the,has%20been%20apprvoed%20for%20use.
EUR-Lex, Access to European Union Law, Document 51977PC0304. Proposal for a Council Directive amending for the first time Directive 74/329/EEC on the approximation of the laws of the Member States relating to emulsifiers, stabilizers, thickeners ang gelling agents for use in foodstuffs (submitted to the Council by the Commission) Dated Jul. 4, 1977. 12 pages. Website: eur-lex.europa.eu/legal-content/EN/TXT/?uri=CELEX%3A51977PC0304&qid=1685448865117.
Firdaus S et al. "Green synthesis of silver nanoparticles using Carica Papaya fruit extract under sunlight irradiation and their colorimetric detection of mercury ions", 2nd International Symposium on Frontier of Applied Physics, IOP Conf Series: Journal of Physics: Conf. Series 817 (2017) 012029. 6 pages. Doi: 10.1088/1742-6596/817/1/012029.
"Food additives" from European Food Safety Authority, Downloaded Jul. 21, 2023. 9 pages. Website: www.efsa.europa.eu/en/topics/topic/food-additives.
"Food additives" from European Food Safety Authority (EFSA), Downloaded though The Wayback Machine for Jul. 17, 2017. 2 pages. Website: www.efsa.europa.eu/en/topics/topic/food-additives.
Geisser, P. et al. Review: The Pharmacokinetics and Pharmacodynamics of Iron Preparations. Pharmaceutics, (Jan. 2011) 3, pp. 12-33. Doi.org/10.3390/pharmaceutics3010012. Website: mdpi.com/journal/pharmaceutics.
Geisser, Peter. Safety and Efficacy of Iron(III)-hydroxide Polymaltose Complex. Arzneimittel-Forschung (Drug Research) 2007: 57 (6a): 439-452.
Gupta A., et al. "Dialysate iron therapy: Infusion of soluble ferric pyrophosphate via the dialysate during hemodialysis" Kidney International (1999); 55(5):1891-1898.
"Iron polymaltose" from Wikipedia, Downloaded: Jul. 23, 2023. 5 pages. Website: en.wikipedia.org/wiki/Iron_polymaltose.
Search of Search Food Additives Database for "E473" from European Food Safety Authority, Downloaded Jul. 21, 2023. 3 pages. Website: food.ec.europa.eu/safety/food-improvement-agents/additives/database_en.

(56) References Cited

OTHER PUBLICATIONS

SiderAL product page on Pharmanutra website. 2 pages. Printed Jul. 21, 2023. Website: www.pharmanutra.it/en/brand/pharmanutra/sideral/.
Sideral.it website. Printed May 19, 2023. 11 pages.
Toblli, J.E. et al., Iron(III)-hydroxide Polymaltose Complex in Iron Deficiency Anemia. Review and Meta-analysis. Arzneimittel-Forschung (Drug Research) 2007: 57 (6a): 431-438.
Advisory Action for U.S. Appl. No. 16/631,426, filed Jan. 15, 2020 on behalf of Pharmanutra S.P.A. Mail Date: Dec. 20, 2022. 4 Pages.
Aoun, M. et al. "High Dephosphorylated-Uncarboxylated MGP in Hemodialysis patients: risk factors and response to vitamin K2, A pre-post intervention clinical trial", BMC Nephrology, Jun. 2017, vol. 18, 191. 10 pages.
Chung, B. et al. "Oncostatin Mis a potent inducer of hepcidin, the iron regulatory hormone", *The FASEB Journal*, Jun. 2010, vol. 24, 2093-2103.
Decision of Rejection for Japanese Application No. 2020-502672 filed on Jul. 26, 2018 on behalf of Pharmanutra S.P.A. Dated Jan. 4, 2023. 9 pages.
Liu, H.Z. et al. "The U937 cell line induced to express CD14 protein by 1,25-dihydroxyvitamin D3 and be sensitive to endotoxin stimulation" *Hepatobiliary Pancreat. Dis. Int.* 2005, vol. 4, No. 1, 84-89.
McCarty, M.F. et al. "Bioavailable dietary phosphate, a mediator of cardiovascular disease, may be decreased with plant-based diets, phosphate binder, niacin, and avoidance of phosphate additives", Nutrition, (Jul.-Aug. 2014), vol. 30, Issues 7-8, pp. 739-747. ISSN 0004771923,.
Nicoll, R. et al. "A Review of the Effect of Diet on Cardiovascular Calcification", Int. J. Mol. Sci., (2015), vol. 16, pp. 8861-8883. ISSN 0004771926.
Non-Final Office Action for U.S. Appl. No. 16/631,426, filed Jan. 15, 2020 on behalf of Pharmanutra S.P.A. Mail Date: Feb. 2, 2023. 17 Pages.
Sonou, T. et al., "Magnesium prevents phosphate-induced vascular calcification via TRPM7 and Pit-1 in an aortic tissue culture model". Hypertension Research, (2017), vol. 40, pp. 562-567. ISSN 0004771924.
Wikipedia page for "International Numbering System for Food Additives" dated Dec. 22, 2016. (16 pp).
Wikipedia page for "E number" dated Jul. 17, 2017. (29 pp).
Notice of Reasons for Refusal for Japanese Application No. 2021-570463 filed May 27, 2020. Mailed on May 7, 2024. Original and Machine translation. 13 pages.
Bagirova, V.L. et al. (1998) No. 6. C. 34-36. Russian original + English extract. 8 pages. (D6).
Barot, B.S. et al. Physicochemical and structural characterization of iron-sucrose formulations: a comparative study. Pharmaceutical Development and Technology. (Published online May 23, 2013) 19 (5): 513-520. 9 pages.
Final Office Action for U.S. Appl. No. 16/631,426, filed Jan. 15, 2020 on behalf of Pharmanutra S.P.A. Mail Date: Nov. 16, 2023. 17 Pages.
First Notification of Office Action for Chinese Application No. 202080039453.9 on behalf of Alesco S.R.L Pharmanutra S.P.A. Issued on Feb. 3, 2024. 3 pages. English translation only.
First Notification of Office Action for Chinese Application No. 202080039535.3 on behalf of Alesco S.R.L Pharmanutra S.P.A. Issued on Feb. 2, 2024. 9 pages. Original + English translation.
First Notification of Office Action for Chinese Application No. 202080039600.2 on behalf of Alesco S.R.L Pharmanutra S.P.A. Issued on Feb. 2, 2024. 10 pages. Original and English translation.
Gomez-Ramirez, Susana et al. Sucrosomial® Iron: A New Generation Iron for Improving Oral Supplementation. Pharmaceuticals. (2018). 11, 97. 23 pages. DOI:10.3390/ph11040097. Website: mdpi.com/journal/pharmaceutical.
Search Report from The Intellectual Property Office of Singapore for Application No. 11202112774X filed on May 27, 2020. Mailed on Aug. 17, 2023. 2 pages. English only.
Search Report from The Intellectual Property Office of Singapore for Application No. 11202112779Y filed on May 27, 2020. Mailed on Aug. 17, 2023. 2 pages. English only.
The Eurasian Patent Office Application No. 202193083/28, Conclusion on patentability of the invention. Mailed on Dec. 19, 2022. 11 pages. Russian and partial English translation.
The Eurasian Patent Office Application No. 202193083/28, Conclusion on patentability of the invention. Mailed on Jul. 19, 2023. 18 pages. Russian and partial English translation.
Wikipedia, The Free Encyclopedia, "Pourbaix diagram", (Dec. 11, 2017). Downloaded on Mar. 29, 2024. 8 pages.
Wikipedia, The Free Encyclopedia, "Sucrose", (Dec. 31, 2017). Downloaded on Mar. 29, 2024. 24 pages.
Wikipedia, The Free Encyclopedia, "Sucrose esters", (Nov. 16, 2017). Downloaded on Mar. 29, 2024. 7 pages.
Written Opinion from The Intellectual Property Office of Singapore for Application No. 11202112774X filed on May 27, 2020. Mailed on Aug. 21, 2023. 7 pages. English only.
Written Opinion from The Intellectual Property Office of Singapore for Application No. 11202112779Y filed on May 27, 2020. Issued on Aug. 21, 2023. 7 pages. English only.
"Converting Units of Measure for Folate, Niacin, and Vitamins A, D, and E on the Nutrition and Supplement Facts Labels: Guidance for Industry", U.S. Dept of Health and Human Services, Food and Drug Administration, Center for Food Safety and Applied Nutrition, Aug. 2019. 31 pages. Website: www.fda.gov/FoodGuidances.
European Food Safety Authority (EFSA), Scientific Opinion on the Safety of 'Cetyl Myristoleate Complex' as a food ingredient. 8 (7), 1686 (2010). 14 pages.
Non-Final Office Action for U.S. Appl. No. 17/614,294, filed Nov. 24, 2021 on behalf of Alesco S.R.L. et al. Mailed on Aug. 28, 2024. 23 pages.
Non-Final Office Action for U.S. Appl. No. 17/613,719, filed Nov. 23, 2021 on behalf of Alesco S.R.L. et al. Mailed on Sep. 18, 2024. 20 pages.
Non-Final Office Action issued for U.S. Appl. No. 17/613,886, filed Nov. 23, 2021 on behalf of Alesco S.R.L. and Pharmanutra S.P.A. Mailed on Aug. 1, 2024. 25 pages.
Shimoyama, Challenges to Unravel Mechanisms of GERD. Gastroesophageal Reflux Disease. Theory and Research. (Nov. 2018).
Ulatowski, L.M. et al., Vitamin E and neurodegeneration. Neurobiology of Disease, 84 (Dec. 2015), 78-83.

\* cited by examiner

COMPOSITION FOR USE IN THE PREVENTION AND IN THE TREATMENT OF IRON DEFICIENCY

CROSS-REFERENCE TO RELATED APPLICATIONS

This application is a US national stage of international application PCT/IB2018/055634 filed on Jul. 27, 2018, which, in turn, claims priority to Italian application No. 102017000089258 filed on Aug. 2, 2017.

DESCRIPTION

The present invention relates to a composition for use in a method for the preventive or curative treatment of an iron deficiency and pathologies and disorders connected thereto in a subject, wherein said use comprises the administration of the composition to said subject.

According to the definition of the National Kidney Foundation (USA), chronic kidney disease (CKD) refers to every pathological condition that affects the kidney and causes, or may cause, progressive and complete loss of kidney function or complications deriving from reduced kidney function. The main causes of CKD are diabetes and high arterial blood pressure, which are responsible for two thirds of the cases.

CKD is defined, based on the guidelines of the National Kidney Foundation, according to the presence or absence of kidney damage and kidney function impairment, irrespective of the causes, with reference to such parameters as the glomerular filtration rate (GFR) and arterial blood pressure.

High arterial blood pressure can also be caused by CKD. Other frequent complications of CKD are cardiovascular and skeletal disorders, metabolic abnormalities, neuropathy and anaemia due, at least in part, to reduced renal production of the hormone erythropoietin.

In general, anaemia is a pathological condition characterized by a decrease in the mass of red blood cells to below the values considered normal. In medical practice, anaemia is defined by the reduction in the quantity of haemoglobin or in the haematocrit value (percentage of red blood cells in a blood sample after centrifugation), or both.

Anaemia is the result of a vast array of causes which may be isolated, but more often coexist. Overall, the most significant contribution to the onset of anaemia is given by iron deficiency (sideropenia), so much so that iron deficiency and anaemia are often used as synonyms.

Subjects with CKD generally present with moderate to severe anemic conditions and require the administration of iron supplements and erythropoiesis stimulating agents (ESAs). However, subjects with CKD commonly respond poorly to erythropoiesis stimulation. It has been hypothesised that the cause of this poor response is the hormone hepcidin.

Iron has a fundamental role in a large number of metabolic processes and is an essential element for living organisms. One of the hormones that regulate iron homeostasis is hepcidin, which is synthesised and secreted mainly by hepatocytes. The expression of hepcidin is mediated by bone morphogenetic proteins (BMPs) and the JAK2/STAT3 metabolic pathway.

The expression of hepcidin is increased in response to a presence of iron stores, inflammation and cellular stress correlated to the endoplasmatic reticulum (ER stress) and decreases in the event of anaemia, hypoxia and oxidative stress and during erythropoiesis.

Hepcidin was initially identified as a peptide with an antibacterial action and designated LEAP-1 (liver-expressed antimicrobial protein); its activity in iron homeostasis was observed at a later time.

Hepcidin, whose levels increase in the event of inflammation, binds to ferroportin and begins to degrade it, thereby inducing a decrease in the level of iron in circulation.

Subjects with CKD or ongoing inflammations (e.g. chronic intestinal inflammations, neoplasms) have high plasma levels of hepcidin.

Recent scientific publications suggest that vitamin D could have a role in regulating hepcidin, reducing the concentration thereof and increasing, accordingly, the levels of iron in the blood (Smith, E. M.; Tangpricha, V. Curr Opin Endocrinol Diabetes Obes 2015, 22 (6), 432-438).

It is well known that iron therapy is an iron-based therapy indicated for treating conditions of an absolute or relative iron deficiency in the body: generally speaking, sideropenic anaemias (including possible iron supplementation during pregnancy).

Iron therapy may be administered both orally, which enables iron to be absorbed through intestinal absorption, and parenterally, which enables absorption through a route other than intestinal absorption, such as, for example, intramuscularly or intravenously. Monitoring of iron therapy is carried out with blood chemistry tests, such as, for example, a blood count and ferritin tests.

It is also well known that the oral administration (per os) of compositions based on iron salts has many limits, such as the scant absorption of iron salts (low bioavailability), and contraindications which limits its use, including gastrointestinal side effects, such as constipation and epigastralgia, which may be of a severe entity.

The main contraindications are represented by: peptic ulcer, gastritis, ulcerous colitis and malabsorption.

In the course of anaemia due to a functional iron deficiency (or inflammatory anaemia or chronic anaemia of inflammation), as a result of the increased synthesis of hepcidin, the intestinal absorption of iron is further reduced. For this reason, supplementation with conventional oral iron is not useful. Today in these cases it is necessary to administer the iron parenterally, which, besides requiring an extremely accurate dose in order to avoid hemosiderosis (overdose), which can lead to convulsions, collapse and coma, has many side effects, including palpitations, tachycardia, diarrhoea, metabolic and taste disorders, headache, skin rash, hypertension and pulmonary oedema. It follows that there is a need for a composition comprising iron which is suitable for oral administration and capable of increasing the haemoglobin values also in subjects with inflammatory anaemia.

There is also a felt need to be able to have a treatment making it possible to prevent or treat pathological states and disorders linked to an iron deficiency, such as anaemia associated with CKD, in a highly effective manner and with fewer side effects compared to treatment with the currently available compositions.

As a solution to said need, the present invention provides a composition for use according to the appended claims.

The subject matter of the present invention relates to a composition comprising or, alternatively, consisting of an effective amount of a mixture which comprises at least:
  (a) one group D vitamin, or analogues and derivatives thereof, and
  (b) an iron (III) oxide, complex or salt;
  and, optionally, (c) pharmaceutical or food grade excipients, additives and/or co-formulants for use in a method for the preventive or curative treatment of an iron deficiency and pathologies and disorders connected thereto in a subject, wherein said use comprises the administration of the composition to said subject.

The subject matter of the present invention relates to a pharmaceutical composition, dietary supplement or medical device comprising or, alternatively, consisting of an effective amount of a mixture which comprises at least (a) one group D vitamin and (b) an iron (III) oxide, complex or salt, and pharmaceutical or food grade excipients, additives and/or co-formulants.

The subject matter of the present invention relates to a composition (pharmaceutical composition, dietary supplement or composition for a medical device) comprising:
  a mixture which comprises or, alternatively, consists of:
  (a) one group D vitamin, or analogues and derivatives thereof, and
  (b) an iron (III) oxide, complex or salt; and, optionally, pharmaceutical or food grade excipients, additives and/or co-formulants;
  wherein said iron (III) oxide, complex or salt is in association with sucrose fatty acid esters (or sucresters) and lecithin (called sucrosomial iron).

The subject matter of the present invention relates to a composition (pharmaceutical composition, dietary supplement or composition for a medical device) comprising:
  a mixture which comprises or, alternatively, consists of:
  (a) one group D vitamin, or analogues and derivatives thereof, and
  (b) an iron (III) oxide, complex or salt; and, optionally, pharmaceutical or food grade excipients, additives and/or co-formulants;
  wherein said iron (III) oxide, complex or salt is in association with sucrose fatty acid esters (or sucresters) and lecithin (called sucrosomial iron); wherein said composition is for use in a method for the preventive or curative treatment of an iron deficiency and pathologies and disorders connected thereto in a subject in the need thereof.

Preferred embodiments of the present invention will emerge clearly from the detailed description that follows and are specified in the appended claims.

Following extensive experimentation, the inventors have developed a composition comprising an association of an iron oxide, complex or salt, optionally in sucrosomial form (as defined below), and a group D vitamin, which is capable of improving the anaemia caused by the condition of chronic inflammation, particularly in subjects affected by chronic kidney disease (CKD).

FIG. 1 shows the levels of IL-6 in U937 cells after 6 hours of treatment. The type of treatment (no LPS: untreated cell (LPS: lipopolysaccharide) is shown on the x axis; LPS: cells treated with LPS alone; Sucro Fe: cells treated with LPS and sucrosomial iron (as defined above or below); Matrixes: cells treated with LPS and sucrosomial matrix (as defined in the experimental part); Pyro Fe: cells treated with LPS and iron pyrophosphate; Sulph Fe: cells treated with LPS and iron sulphate; Vit D+Sucro Fe: cells treated with LPS and Vitamin D in combination with sucrosomial iron (as defined above or below, composition according to the invention); Vit D: cells treated with LPS and vitamin D). The pg/ml of IL-6 produced per million of cells are represented on the y axis. These results represent a mean of two different experiments.

FIG. 2 shows the level of hepcidin produced by HepG2 cells in the supernatant after 18 hours of treatment with the iron compounds, vitamin D and compositions thereof. The type of treatment (no LPS: untreated cell; LPS: cells treated with LPS alone; Sucro Fe: cells treated with LPS and sucrosomial iron (as defined above or below) is shown on the x axis; Matrixes: cells treated with LPS and sucrosomial matrix; Pyro Fe: cells treated with LPS and iron pyrophosphate; Sulph Fe: cells treated with LPS and iron sulphate; Vit D+sucrosomial iron: cells treated with LPS and Vitamin D in combination with sucrosomial iron (as defined above or below, composition according to the invention); Vit D: cells treated with LPS and vitamin D). The ng/ml of hepcidin produced per million of cells are represented on the y axis. These results represent a mean of two different experiments.

Within the scope of the present invention, "method for the treatment" of a pathology or disorder means therapy aimed at restoring the health conditions of a subject, maintaining the existing conditions and/or preventing the worsening of said health conditions.

Within the scope of the present invention, "prevention" of a pathology or disorder means therapy aimed at avoiding the onset of such a pathology or disorder in a subject, also, but not only, as a complication or effect of a pre-existing pathological condition or disorder.

Unless specified otherwise, within the scope of the present invention the percentages and amounts of a component in a mixture are intended to refer to the weight of that component relative to the total weight of the mixture.

Unless specified otherwise, within the scope of the present invention, as regards the ranges of numerical values for a certain characteristic, the indication "from X to Y" comprises the outermost values of the range, i.e. X and Y, as well as all the possible intermediate numerical values.

In the context of the present invention, the term "composition(s)" is meant to include a pharmaceutical composition, a composition for a dietary supplement, a composition for a food product or a composition for a medical device.

Within the scope of the present invention, "group D vitamin" means a compound belonging to a group of liposoluble prohormones of natural origin comprising vitamin D1 (ergocalciferol and lumisterol 1:1), vitamin D2 (ergocalciferol), vitamin D3 (cholecalciferol); vitamin D4 (dihydroergocalciferol), vitamin D5 (sitocalciferol), and the complexes and derivatives and metabolic precursors thereof, such as, without limitation, esters (e.g. acetates), amides and the like and mixtures thereof.

Within the scope of the present invention, "one group D vitamin, or analogues and derivatives thereof" means, as mentioned above, complexes of the compounds belonging to the vitamin D group, protection derivatives, such as compounds belonging to the vitamin D group whose functional groups are protected with suitable protector groups, or metabolic precursors, known to the person skilled in the art.

In the composition according to the present invention, the group D vitamin is preferably cholecalciferol (D3, CAS No. 67-97-0) or ergocalciferol (vitamin D2, CAS No. 50-14-6); more preferably, the group D vitamin is cholecalciferol.

The composition according to the present invention comprises, in addition to at least one group D vitamin, at least one iron (III) oxide, complex or salt, which is suitable for administration to human subjects or for veterinary use.

By way of non-limiting example, said salt can be organic or inorganic, such as a chloride, sulphate, pyrophosphate, citrate, bisglycinate, fumarate, gluconate, ascorbate, and mixtures thereof.

Within the scope of the present invention, "complex" means a coordination complex made up of one or more iron atoms and one or more atoms, ions or molecules that surround them, at least partially, without forming either an ionic or covalent bond (binders or ligands).

The composition according to the invention preferably comprises at least one Fe (III) salt; more preferably, said salt is iron (III) pyrophosphate ($Fe_4 (P_2O_7)_3$).

In a preferred embodiment, in the composition according to the invention the iron (iron III) oxide, complex or salt is in a "sucrosomial" form or forma "sucrosomiale" (Sucrosomiale®; Sucrosomial®; registered Trademarks in the name of PHARMANUTRA S.P.A. and ALESCO S. R. L.) i.e. in the form of a complex made up of sucresters (sucrose fatty acid esters) and lecithin, which facilitate its delivery and the absorption by the subject. In other words, in the composition according to the invention the iron (III) oxide, complex or salt is in association with sucrose fatty acid esters, i.e. sucresters (E473), lecithin and, optionally, pregelatinized starch.

In the context of the present invention, the term "sucrosomial iron" indicates a formulation of an iron mineral, namely, the aforesaid iron (III) oxide, complex or salt, in which said iron mineral is processed and formulated by means of the preparation methods described below. Preferably, when an iron (III) salt, such as, for example, iron (III) pyrophosphate, is processed and formulated together with other substances, by means of the preparation methods described above, a sucrosomial iron is obtained.

In other words, in the composition according to the invention the iron (III) oxide, complex or salt is formulated in association with sucrose fatty acid esters or sucresters (E473), lecithin and, optionally, gelatinized or pregelatinized starch.

In the context of the present invention, the terms "iron (III) formulated in association with sucresters and lecithin" and "iron (III) in association with sucresters and lecithin" are interchangeable in meaning.

As a non-limiting example, when the iron oxide, complex or salt is in "sucrosomial" form in the composition of the present invention it can be prepared according to one of the methods described in WO 2014/009806 A1. More specifically, a first method for preparing "sucrosomial iron" in solid form is described in WO 2014/009806 A1 from page 7 line 1 to page 8 line 20, incorporated in the present application by reference, a second method for preparing "sucrosomial iron" in solid form is described from page 8 line 22 to page 10 line 21, incorporated in the present application by reference. Finally, a method for preparing "sucrosomial iron" in liquid form is described in WO 2014/009806 A1 from page 12 line 21 to page 14 line 3, incorporated in the present application by reference.

In a preferred embodiment, the composition according to the invention comprises:
- a mixture which comprises or, alternatively, consists of (a) one group D vitamin, preferably cholecalciferol (vitamin D3), and (b) an iron (III) oxide, complex or salt in sucrosomial form (as defined in the present invention), i.e. an iron (III) oxide, complex or salt formulated in association with sucrose fatty acid esters or sucresters, lecithin and, optionally, gelatinized or pregelatinized vegetable starch.

It was found that the iron salt or oxide or complex in sucrosomial form has improved palatability and is easily absorbable also by particularly sensitive subjects, such as pregnant women.

Said iron (III) in sucrosomial form comprises, in association with said iron (III) oxide, complex or salt, a lecithin as described below.

Lecithin is a food additive-E322 (Directive No. 95/2/EC of 20.2.95 published in O. J. No. L61 of 18.3.95). Due to its physicochemical properties, lecithin primarily plays an emulsifying function and, being also rich in natural antioxidant substances, has a secondary antioxidant function as well. Directive No. 2008/84/EC of 27 Aug. 2008 (published in the O. J. of the European Union No. L253) establishes the purity criteria that lecithin has to meet in order to be considered of food grade quality (E322): Acetone-insoluble (essentially the active part of lecithin): 60% min.; Humidity: 2% max.; Acid number: 35 max.; Peroxide value: 10 max.; Toluene-insoluble (essentially impurities): 0.3% max.

From a chemical point of view, lecithin is a mixture of phosphoric acid, choline, fatty acids, glycerol, glycolipids, triglycerides and phospholipids. Phospholipids represent the main components thereof; they are derived from the triglyceride structure, wherein a fatty acid is replaced by a phosphate group, which imparts a negative charge, and thus, polarity to the molecule; this molecule has the generic name of phosphatide. A more complex organic molecule, usually serine, choline, ethanolamine, inositol or a single hydrogen atom, is bound to the phosphate group through an ester bond, giving rise to a phospholipid named phosphatidylserine, phosphatidylcholine, phosphatidylethanolamine, phosphatidylinositol or phosphatidic acid, respectively. In a stricter sense of lecithin, phosphatidylcholine is often designated. Phospholipids are characterized by a polar, water-soluble head, which dissolves well in water, whereas the two saturated fatty acids represent the two non-polar, not water-soluble but lipophilic tails. Molecules of this type are called amphipathic and in the presence of water and fats they arrange themselves between the fatty and water molecules, emulsifying them. Lecithin is a natural emulsifier.

The composition of the present invention contains neither a hydrolyzed lecithin nor an enzymatically hydrolyzed lecithin.

The lecithin used is a non-hydrolyzed lecithin powder and can be a sunflower or maize or soya lecithin. The lecithin used is a lecithin powder having a water content comprised from 1.5 to 4.5%, preferably from 2 to 4%, even more preferably from 2.5 to 3.5%. Advantageously, the lecithin used is a sunflower lecithin powder.

In one embodiment, the sunflower lecithin contains an amount of glucose comprised from 20 to 60%, preferably from 30 to 50%, for example about 45% by weight, such as, without limitation, in the product Lecico Sun™ CG 450 from the Lecico GmbH Company-Germany or Lecifis Sun™ CG 45M007501 from Alesco S. r. l.

A sunflower lecithin usable in the context of the present invention may have the following composition by weight (physiochemical analysis): sunflower lecithin from 40 to 50%, carbohydrates from 40 to 50% (for example about 42%), proteins from 6 to 10%, ash from 3 to 8%, humidity from 2 to 5% and another glidant from 0.5 to 1.5%.

Lecithin is present in the solid composition of the present invention in an amount comprised from 0.1 to 1.5%, preferably from 0.4 to 1.0%, even more preferably from 0.50 to 0.8% by weight.

Advantageously, the iron (III) salt is iron pyrophosphate and the lecithin is from sunflower and/or of maize.

Said iron (III) in sucrosomial form comprises, in association with said iron (III) oxide, complex or salt, in addition to said lecithin described above, a sucrester as described below.

The solid or liquid composition of the present invention further comprises, in association with a lecithin as described above, a sucrose ester or sucrester.

Sucresters are obtained by fatty acid esterification or transesterification of fatty acid methyl esters with carbohydrates, generally sucrose and other polysaccharides, for this reason they are also referred to as fatty acid sucrose esters (alternatively called sucrose fatty acid esters or carbohydrate fatty acid esters; briefly, sucrose esters). The physicochemical properties of these compounds depend on the number and type of esterified fatty acids. The code E473 indicates that sucresters are food additives permitted by European Union legislation and regulated by Italian ministerial decree D. M. 209 of 27 Feb. 1996. They are essentially emulsifiers and are added in order to obtain a better stabilization between an aqueous phase and a fatty phase.

Sucrose esters are sucresters (E473) and are used in the composition of the present invention with non-ionic surfactants having an HLB value of about 14-18, advantageously an HLB value of about 15 or 16, and are used as emulsifiers.

In one embodiment, the sucrester E473 contains 70% monoesters, obtained by sucrose esterification with fatty acids of vegetable origin (stearic and palmitic).

A sucrester usable in the context of the present invention may have the following composition by weight: total ester content of at least 90%; free fatty acid (such as oleic acid) content no greater than 3%; free sucrose content no greater than 2%; humidity no greater than 4%; acid value no greater than 5.

Sucrose esters (sucrose fatty acid esters) or sucresters are present in the solid composition in an amount comprised from 10 to 20%, preferably from 12.5 to 18.5%, even more preferably from 16 to 18.0% by weight.

The solid or liquid composition for oral use of the present invention does not contain an ester of a fatty acid and diglycerol (diglycerol fatty acid ester).

The composition of the present invention does not contain an ester of a fatty acid and diglycerol (diglycerol fatty acid ester).

The solid or liquid composition of the present invention, in addition to a vitamin D, preferably comprises iron (III) salts, complexes or oxides, a lecithin E322 (not hydrolyzed, much less enzymatically hydrolyzed) and sucrose esters, or sucresters, E473 (sucrosomial iron), in an amount by weight as specified above.

In a preferred embodiment, the composition of the present invention comprises a mixture which comprises or, alternatively, consists of (a) at least one group D vitamin, preferably cholecalciferol (vitamin D3) and (b) iron (III) pyrophosphate in association with a lecithin E322 (not hydrolyzed, much less enzymatically hydrolyzed), preferably from sunflower, and sucrose fatty acid esters E473, or sucresters E473 (sucrosomial iron of iron pyrophosphate), in an amount by weight as specified above.

Said iron (III) in sucrosomial form can also comprise, in association with said iron (III) oxide, complex or salt, and in addition to said sucresters and said lecithin, a gelatinized or pregelatinized vegetable starch as described below.

In a preferred embodiment, the solid or liquid composition of the present invention can further comprise a gelatinized or pregelatinized vegetable starch.

The vegetable starch is selected from rice starches or maize starches. Advantageously, the starch is a rice starch. Advantageously, the rice starch is a gelatinized or pregelatinized native rice starch.

A pregelatinized rice starch usable in the composition of the present invention may have the following physicochemical characteristics: humidity no greater than 7%; protein content no greater than 1%; ash content no greater than 1%; pH (10% solution) comprised from 5.5 to 7.5, density 0.40-0.48 $g/cm^3$; minimum starch content 97% and fat content no greater than 0.1%. The gelatinized or pregelatinized vegetable starch is present in the solid composition in an amount comprised from 15 to 40%, preferably from 20 to 35, even more preferably from 25 to 30% by weight, relative to the total weight of the sucrosomial iron (i.e. the iron complex, oxide or salt+lecithin+sucresters E473) present.

By way of non-limiting example, said composition (or sucrosomial iron) comprising vegetable starch can be prepared according to one of the methods described in WO 2014/009806 A1 (the paragraphs of WO 2014/009806 A1 cited above are incorporated in the present application by reference).

In one embodiment, the solid or liquid composition of the present invention comprises, in addition to a group D vitamin, at least one iron (III) salt or oxide or complex, a lecithin E322 (not hydrolyzed, much less enzymatically hydrolyzed), sucrose esters or sucresters E473 and a vegetable starch, in the amounts by weight specified above.

In a preferred embodiment, the solid or liquid composition of the present invention comprises, in addition to a vitamin D, at least one iron (III) salt or oxide or complex from pyrophosphate, a sunflower lecithin (E322) (not hydrolyzed, much less enzymatically hydrolyzed), sucrose esters or sucresters E473 and a pregelatinized rice starch (sucrosomial iron), in the amounts by weight specified above.

In a preferred embodiment, the composition of the present invention comprises a mixture which comprises or, alternatively, consists of (a) cholecalciferol (vitamin D3) and (b) an iron (III) oxide, complex or salt, preferably iron pyrophosphate, in association with said lecithin (described above), said sucrester (described above) and a gelatinized or pregelatinized vegetable starch (sucrosomial iron), in the amounts by weight specified above.

It remains understood that, in the treatment according to the invention, the administration of the active ingredients (a)-(b), and, if present, the other ingredients, can take place simultaneously, for example in a single formulation, or in rapid sequence, for example with two or more formulations taken by the subject in any order, in a sequence closely spaced in time (e.g. within 1 to 10 minutes) in two distinct compositions.

The composition according to the present invention can be for use in human subjects or for veterinary use, for example, but without limitation, in pets such as cats or dogs, or in other mammals. The composition according to the present invention is preferably for use in humans.

In one embodiment, the administration of the composition to the subject takes place orally, for example in the form of a pill, tablet, which may also be coated, a capsule, solution, suspension, syrup, food containing probiotic bacteria, or in any other form known to the person skilled in the art.

It remains understood that the administration of the active ingredients according to the invention can take place simultaneously, for example in a single formulation, or in rapid sequence, for example with two or more formulations taken by the subject in any order, in a sequence closely spaced in time (e.g. within 1 to 10 minutes) in two distinct compositions.

The composition or the composition for use according to the present invention can comprise, in addition to an iron (iron (III)) oxide or complex and vitamin D, at least one inert ingredient, such as at least one excipient among the ones commonly used and known to the person skilled in the art.

"Inert ingredient" means any substance, or combination of substances, auxiliary to the production of a pharmaceutical, dietary or nutraceutical form, which is to be found in the finished product and is not the active ingredient, although it can modify the stability, release or other characteristics thereof.

Non-limiting examples of such ingredients, as is known to the person skilled in the art of formulations in the pharmaceutical, nutraceutical or food industry, are excipients such as diluents, absorbents, lubricants, colourants, surfactants, antioxidants, sweeteners, binders, anti-caking agents, acidifying agents, disaggregating agents and the like.

In one embodiment, the composition or the composition for use according to the present invention comprises or may comprise, in addition to at least one iron (iron (III)) salt or oxide and a vitamin D, at least one further active ingredient of natural or synthetic origin. Non-limiting examples of such active ingredients are: Vitamin C, omega-3 fatty acids: EPA, DHA; Vitamin B6, Vitamin B12, folic acid, and mixtures thereof.

The present invention provides a composition, as defined in the appended claims or in the present description, for use in a method for the preventive or curative treatment of anaemia of inflammation, preferably deriving from or correlated to chronic kidney disease (CKD), nephropathy, neoplasms, chronic inflammatory intestinal diseases, ulcerous colitis, Crohn's Disease, coeliac disease, fibromyalgia, heart failure, more preferably correlated to CKD.

In one aspect, the present invention provides a method for the preventive or curative treatment of anaemia of inflammation, preferably correlated to chronic kidney disease (CKD), nephropathy, neoplasms, chronic inflammatory intestinal diseases, ulcerous colitis, Crohn's Disease, coeliac disease, fibromyalgia, heart failure, more preferably correlated to CKD, comprising administration to a subject of the composition as defined in the appended claims.

Anaemia of chronic disease (ACD) or anaemia of phlogosis or inflammation, or anaemia of chronic disorders is a hypoproliferative form of anaemia that is observed in the course of chronic diseases, for example in cases of chronic infection, such as bacterial endocarditis, osteomyelitis, HIV/AIDS, hepatitis B or C, autoimmune disorders such as lupus erythematous and Crohn's disease, rheumatoid arthritis and ulcerous colitis, arthritis, chronic kidney disease (CKD) and tumour-related disorders. In the most severe cases, the therapy presently indicated for anaemia of chronic disease includes blood transfusions or the administration of substances that stimulate erythropoiesis, such as erythropoietin or darbepoietin.

In one embodiment, the composition according to the invention is for use in a method for the preventive or curative treatment of an iron deficiency or anaemia of inflammation and pathologies and disorders connected thereto in a subject affected by chronic kidney disease (CKD), nephropathy, neoplasms, chronic inflammatory intestinal diseases, ulcerous colitis, Crohn's Disease, coeliac disease, fibromyalgia, heart failure, more preferably in a subject affected by chronic kidney disease (CKD).

In a preferred embodiment, the composition according to the invention is for use in a method for the preventive or curative treatment of an iron deficiency or anaemia of inflammation and pathologies and disorders connected thereto in a subject affected by a nephropathy, preferably in a subject affected by chronic kidney disease (CKD).

The composition of the present invention, as defined above, can be a pharmaceutical composition, a food or a dietary supplement or a composition for a medical device.

In one aspect, the present invention provides a pharmaceutical composition, dietary supplement or medical device comprising or, alternatively, consisting of an effective amount of a mixture which comprises at least (a) one group D vitamin and (b) an iron (III) oxide, complex or salt, and
 pharmaceutical or food grade excipients, additives and/or co-formulants.

In the context of the present invention, the term "medical device" is used with the meaning according to Italian Legislative Decree no. 46 of 24 Feb. 1997, i.e. it indicates a substance or another product, whether used alone or in combination, intended by the manufacturer to be used for human beings for the purpose of diagnosis, prevention, monitoring, treatment or alleviation of a disease, and which does not achieve its principal intended action in or on the human body by pharmacological, immunological or metabolic means, but which may be assisted in its function by such means.

The sucrosomial iron, as defined above, can be in solid or liquid form; it is preferably in solid form.

The composition of the present invention, as defined above, can be in solid, liquid or semisolid form; it is preferably in solid form.

The pharmaceutical composition, dietary supplement or medical device of the present invention can be solid, liquid or semisolid, for example as a suspension or gel, and can be in any form known to the person skilled in the art of the food, pharmaceutical or nutraceutical formulations, such as, by way of non-limiting example, in the form of a capsule, tablet, or powder that is at least partially dissolvable in the mouth or water soluble, granules, pellets or microparticles optionally contained in a sachet or in a capsule or mini-tablet, a liquid or semisolid preparation, gel, suspension, solution, two-phase liquid system and equivalent forms.

The pharmaceutical composition, dietary supplement or medical device of the present invention is preferably in solid form.

The subject matter of the present invention further relates to the non-therapeutic use of the composition of the present invention (as defined above) for a non-therapeutic treatment of iron deficiencies and pathologies or disorders connected thereto in a subject who requires said non-therapeutic treatment.

Said non-therapeutic use of the composition of the present invention is preferably for the non-therapeutic treatment of iron deficiencies and pathologies and disorders connected thereto in a subject affected by chronic kidney disease (CKD), nephropathy, neoplasms, chronic inflammatory intestinal diseases, ulcerous colitis, Crohn's Disease, coeliac disease, fibromyalgia, heart failure, more preferably in a subject affected by chronic kidney disease (CKD) and/or nephropathy, preferably wherein the nephropathy is chronic kidney disease (CKD).

Embodiments of the present invention are set forth below (RPn):

RP1. A composition comprising or, alternatively, consisting of an effective amount of a mixture which comprises at least:

(a) one group D vitamin, or analogues and derivatives thereof, and (b) an iron (III) oxide, complex or salt; and, optionally, (c) pharmaceutical or food grade excipients, additives and/or co-formulants for use in the preventive or curative treatment of an iron deficiency and pathologies and disorders connected thereto in a subject, wherein said use comprises the administration of the composition to said subject.

RP2. The composition for use according to RP1, wherein the at least one group D vitamin is vitamin D3, i.e. cholecalciferol.

RP3. The composition for use according to at least one of the preceding RPs, wherein the iron salt is iron pyrophosphate.

RP4. The composition for use according to RP3, wherein the iron pyrophosphate is in association with sucrose fatty acid esters, i.e. sucresters (E473), lecithin and, optionally, pregelatinized starch.

RP5. The composition according to at least one of the preceding RPs for use in the curative or preventive treatment of anaemia of inflammation, preferably deriving from or connected to at least one among nephropathy, neoplasms, chronic inflammatory intestinal diseases, ulcerous colitis, Crohn's Disease, coeliac disease, fibromyalgia and heart failure.

RP6. The composition according to at least one of the preceding RPs for use in a subject affected by a nephropathy.

RP7. The composition for use according to RP6, wherein the nephropathy is chronic kidney disease (CKD).

RP8. The composition for use according to at least one of the preceding RPs, wherein said administration takes place via the oral route.

RP9. A pharmaceutical composition, dietary supplement or medical device comprising or, alternatively, consisting of an effective amount of a mixture which comprises at least (a) one group D vitamin and (b) an iron (III) oxide, complex or salt, and pharmaceutical or food grade excipients, additives and/or co-formulants.

The following experimental part provides examples of practical embodiments of the invention, without limiting the scope thereof.

EXPERIMENTAL PART

I) in vitro STUDIES

In order to better understand the role of iron (III) (as a dietary source of iron) and the intake of vitamin D in the inflammatory process, an assessment was made of the expression of hepcidin and other inflammatory markers in treated human hepatocellular carcinoma and monocytic cell lines. The markers studied were interleukin-6 (IL-6), C-reactive protein (CRP) and hepcidin. IL-6 was assessed in the U937 cell line (monocytic cell line), whilst CRP and hepcidin were assessed in the HepG2 cell line (hepatocellular carcinoma cell line).

IL-6 and CRP are typically expressed and evaluated markers during acute inflammation (Rincon, M. "*Interleukin-6: from an inflammatory marker to a target for inflammatory diseases*" Trends in Immunology November 2012, Vol. 33, No. 11, pages 571-577, Pepys, M. P; Hirschfield, G. M. "*C-reactive protein: a critical update*" J. Clin. Invest. 2003, 111:1805-1812). Since lipopolysaccharide (LPS) is a well-known inducer of hepcidin expression in macrophages and hepatocytes (Zughaier, S. M. et al. "The role of vitamin D in regulating the iron-hepcidin-ferroportin axis in monocytes" *J Clin Transl Endocrinol* (2014) e9-e25), in order to stimulate inflammation the cells were treated with lipopolysaccharide (LPS) and then analysed for the production of markers in terms of protein expression in the supernatants of the cells. The aim of this study was to assess the ability of LPS to simulate inflammation in the selected cell lines and to investigate the effect of the compounds containing an iron (III) oxide, complex or salt and D vitamin according to the invention compared to other iron-containing compounds in the stimulated cell lines in terms of IL-6, CRP and hepcidin expression.

MATERIALS 1.1 Cells and Cell Cultures

The U937 cells (monocytic leukaemia cell lines) [Sundström, C.; Nilsson, K. "*Establishment and characterization of a human histiocytic lymphoma cell line* (U-937)" International Journal of Cancer 1976 May 15;17 (5): 565-77] were grown in suspension in the medium RPMI 1640 (Sigma) supplemented with 2 mM glutamine, 10% FBS (EU-approved Euroclone), 100U/ml penicillin and 100 µg/ml streptomycin and were purchased from Sigma. The cells were maintained between 2-9×100,000 cells/ml with 5% $CO_2$ at 37° C.

The HepG2 cells (human hepatoblastoma cell lines) [U.S. Pat. No. 4,393,133] were grown in an adherent culture in ATCC medium, with a supplement of 10% FBS, 100U/ml penicillin and 100 µg/ml of streptomycin and were purchased from ATCC. The cells were maintained between 5-15×100,000 cells/ml with 5% $CO_2$ at 37° C.

PMA (Phorbol 12-myristate 13-acetate) was purchased from Sigma-Aldrich (catalogue number $P_{1585}$-1 MG), dissolved in 1 ml of DMSO (Sigma-Aldrich catalogue number D8418-50 ML) and further diluted to a final concentration of 100 micrograms/ml in a sterile phosphate buffer saline solution (PBS) (Lonza catalogue number 17-516-F).

LPS (Lipopolysaccharides of *Escherichia coli*) was purchased from Sigma-Aldrich (Sigma catalogue number L4391), dissolved in sterile PBS and then diluted in sterile PBS and in the culture medium.

ELISA kit: Diaclone human IL-6 Elisa kit (catalogue number 950.030.096, sensitivity 2 pg/ml); DRG CRP HS ELISA (catalogue number EIA-3954, sensitivity range: 0.1-10 pg/ml); Invitrogen human C-reactive protein ELISA kit (catalogue number #KHA0031, sensitivity range: 10-1200 pg/ml); DRG Hepcidin-25 (bioactive) ELISA (catalogue number EIA-5258, sensitivity range: 0.35-80 ng/ml).

2. Test Setup

In order to establish the best experimental condition, preliminary tests were performed to investigate the cell response to the iron compounds and vitamin D, the optimal concentration of the compounds and the optimal incubation period. The selected experimental condition determined after this step was then applied to assess the response of the inflammatory markers.

2.1 Treatment of the Monocytic Cells and Induction of Macrophages

The U937 cells were treated with PMA as previously described (Shelley, C. S. et al. "*During Differentiation of the Monocytic Cell Line U937, Puran Mediates Induction of the CDIIc β2 Integrin Gene Promoter*" J Immunol 2002, 168, 3887-3893): in the T25 tissue culture buffers, the U937 wells were treated with 20 ng/ml, 50 ng/ml, 100 ng/ml, 150 ng/ml and 200 ng/ml of PMA in an incomplete RPMI 1640 medium without FBS (without antibiotics or glutamine). After 24 h the medium was replaced with a fresh complete medium, without PMA, and the cells were left to adhere for 72 h (Garrelds, I. M. et al. "*Time dependent production of cytokines and eicosanoids by human monocytic leukaemia U937 cells; effects of glucocorticosteroids*" Mediators Inflamm 1999, 8, 229-235). With the aim of choosing the right concentration to be used for the test, after 72 hours the cells were checked for adhesion and morphological change.

2.2 Stimulation of U937 Cells with LPS

The U937 cells previously treated with 150 ng/ml of PMA were detached with the aid of a cell scraper (Garrelds, I. M. et al. "*Time dependent production of cytokines and eicosanoids by human monocytic leukemia U937 cells; effects of glucocorticosteroids*" Mediators Inflamm 1999, 8, 229-235) and seeded in 6 wells with a cell density of 650,000 cells/ml. The cells were left to adhere for 24 h at 37° C., 5% $CO_2$ and then the medium was replaced with an FBS-free incomplete one (without antibiotics or glutamine) containing 10 ng/ml, 20 ng/ml and 40 ng/ml of LPS from *E. Coli* (Liu, H.-Z. et al. "*The U937 cell line induced to express CD14 protein by 1,25-dihydroxyvitamin D3 and be sensitive to endotoxin stimulation*" Hepatobiliary Pancreat. Dis. Int. 2005, Vol. 4, No. 1, 84-89). The cells were checked after 6 hours and 20 hours in order to select the best concentration to use for the experiments.

2.3 Stimulation of HepG2 Cells with LPS

The HepG2 cells were seeded in a 6-well plate with a cell density of 650,000 cells/ml and left to adhere for 24 hours at 37° C., 5% $CO_2$. After 24 hours, the medium was replaced with an incomplete FBS-free one (without antibiotics) containing 10 ng/ml, 20 ng/ml and 40 ng/ml of LPS from *E. Coli* (Sigma L4391) (Huang, Z. B. et al. "HMGB1 release by human liver L02 and HepG2 cells induced by lipopolysaccharide" *Molecular Medicine Reports* 8:103-112, 2013, Saliou, C. et al. "*Selective inhibition of NF-UB activation by the flavonoid hepatoprotector silymarin in HepG2, Evidence for different activating pathways*" FEBS Letters 1998, 440, 8:12; Chung, B. et al. "*Oncostatin M is a potent inducer of hepcidin, the iron regulatory hormone*", The FASEB Journal 2010, Vol. 24, 2093-2103). The cells were checked after 6 hours and 20 hours in order to select the best concentration to use for the experiments.

2.4 Iron Compounds and Vitamin D

The compounds used for the experiments were: sucrosomial iron (prepared according to one of the methods described in WO 2014/009806 A1 (as previously noted), indicated as Sucro Fe in the figures), sucrosomial matrix (prepared according to one of the methods described in WO 2014/009806 A1 (as noted above) but without iron salts or oxides or complexes), iron pyrophosphate, iron sulphate, vitamin D and vitamin D with sucrosomial iron.

The iron content of the compounds (with the exception of the vitamin D and the sucrosomial matrix) was 30 mg/ml. A 1:100 dilution was performed for all of the compounds in sterile PBS in order to obtain an iron concentration of 300 micrograms/ml. For experimental purposes, the compounds that did not contain iron were diluted with the same dilution ratio as the iron-containing compounds (vitamin D was diluted at the same ratio as Vitamin D and sucrosomial iron and the sucrosomial matrix was diluted at the same dilution ratio as sucrosomial iron). The final iron concentration used in the experiments has been described elsewhere (Barisani et al. "*Iron overload and gene expression in HepG2 cells: analysis by differential display*" FEBS Letters 2000, 469, 208-212). The compounds (initial dilution of 300 pg/ml) were diluted in an incomplete FBS-free medium (RPMI 1640 for the U937 cells, EMEM for the HepG2 cells) with a dilution factor of 1:6 for a final iron concentration of 50 micrograms/ml. A test was conducted to assess the effect of the compounds on the cell cultures: induced FlepG2 and U937 were seeded a with a cell density of 650,000 cells/ml in 6 wells (final volume 1.5 ml/well). After 24 hours the medium was replaced with a new FBS-free (incomplete) one containing 50 g/ml of iron and after 24 hours the cells were macroscopically checked (visual inspection using a microscope). Given that after 24 hours the cells incubated with the iron treatment showed to be contaminated (black patch moving amidst the cells), the diluted compounds were irradiated under UV light for a total time of 150 minutes before further experiments were undertaken (Berrin Özçelik "*Fungi/Bactericidal and Static Effect of Ultraviolet Light in 254 and 354 nm wavelengths*" Research Journal of Microbiology 2007 2 (1): 42-49).

3. Marker Detection.

3.1 Treatment of Cells and Analysis of the Markers.

The U937 cells, induced with PMA as described above, were seeded in 6 wells at a concentration of 650,000 cells/ml (1.5 ml/well). The plates were incubated for 24 hours at 37° C. and 5% $CO_2$. After the 24-hour medium was replaced with an FBS-free incomplete RPMI 1640 containing 20 ng/ml of LPS. A control well was prepared with an LPS-FBS-free incomplete medium. After 20 hours of incubation at 37° C. and 5% $CO_2$, the medium was replaced with the iron treatment solutions (medium containing 50 g/ml of iron). In the control well, the medium was replaced with an incomplete FBS-free RPMI 1640 medium. Another control well without iron was prepared, replacing a container containing LPS with a fresh FBS-free incomplete medium. After 6, 18 and 24 hours, the supernatants were collected from the wells, centrifuged for 10 minutes at 1000 g, transferred into a new tube and stored a -20° C. for the analysis of IL-6 [Miki, K. et al. "*Extracellular activation of arginase-1 decreases enterocyte inducible nitric oxide synthase activity during systemic inflammation*" Am J Physiol Gastrointest Liver Physiol. 2009; 297 (4): G840-G848]. The cells of each well collected were detached using a scraper and counted using Trypan blue with a Burker counting chamber ("Strober W. "*Trypan blue exclusion test of cell viability*" Curr Protoc Immunol. 2001 May; Appendix 3: Appendix 3B).

The HepG2 cells were seeded in 6 wells at a concentration of 650,000 cells/ml (1.5 ml/well). The plates were incubated for 24 hours at 37° C. and 5% $CO_2$ first. Afterwards, the 24-hour medium was replaced with an incomplete EMEM without FEM, containing 40 ng/ml of LPS. A control well was prepared with an LPS-FBS-free incomplete medium. After 20 hours of incubation at 37° C. and 5% $CO_2$, the medium was replaced with the iron treatment solutions (medium containing 50 g/ml of iron). In the control well, the medium was replaced by an incomplete FBS-free EMEM medium. Another control well without iron was prepared, replacing a container containing LPS with a fresh incomplete FBS-free medium. After 6, 18 and 24 ore, the hours, the supernatants were collected from the wells, centrifuged for 10 minutes at 1000 g, transferred into a new tube and stored a -20° C. for the analysis of hepcidin and CRP. The cells of each well collected were detached using trypsin and counted using Trypan blue with a Bürker counting chamber.

An analysis of the marker was performed using commercially available ELISA kits. Before the ELISA analysis was started, the samples were thawed at room temperature for 1 hour and mixed. The ELISA analysis was performed following the instructions of the kit manufacturers. The plates were read using a Molecular Devices 340PC384 microplate reader and the data were analysed by means of SoftmaxPro software using a data reduction function with 4-parameter logistic curve fitting.

4. Results of the Setup 4.1 Induction of Macrophages

For the purpose of conducting an analysis on the inflammation markers, the U937 cells had to be induced to macrophages by means of a treatment with Phorbol-12-myristate-13-acetate (PMA). The treatment was directly performed in T25 tissue culture columns cultured with 5×105/ml of cells. 24 hours after the treatment, the cells began to adhere and the medium was replaced by a complete one. 48 h after the treatment with PMA, the U937 cells began to change their morphology in terms of increase in cytoplasmic volume and cytoplasmic protrusions. Five concentrations of PMA were tested (20 ng/ml, 50 ng/ml, 100 ng/ml, 150 ng/ml and 200 ng/ml PMA) and the 150 ng/ml enabled a better induction compared to the other concentrations in terms of cell adhesion and change in morphology. This concentration was confirmed in 2 tests.

4.2 LPS Stimulation

It is well known that LPS is capable of stimulating HepG2 cells [Villaroel et al. "*Interleukin 6 and lipopolysaccharide modulate hepcidin mRNA expression by HepG2 cells*" Biol Trace Elem Res. 2012 December; 150 (1-3): 496-501] and U937 [Liu, H.-Z. et al. "*The U937 cell line induced to express CD14 protein by 1,25-dihydroxyvitamin D3 and be sensitive to endotoxin stimulation*" Hepatobiliary Pancreat. Dis. Int. 2005, Vol. 4, No. 1, 84-89]. In order to understand whether LPS is capable of stimulating the production of IL-6 in the U937 cells induced by PMA and CRP and hepcidin in the HepG2 cells, a treatment was performed on the 2 cell lines for 6 and 20 hours with 10 ng/ml, 20 ng/ml and 40 ng/ml of LPS. The U937 cells seemed to have suffered with the LPS concentration of 40 ng/ml at 6 and 20 hours (there was a small amount of cells in the wells at the end of the treatment) and were discarded.

The HepG2 cells were more resistant to the LPS treatment at all concentrations and at both times. After the visual check, the concentration chosen to be analysed via ELISA was 20 ng/ml for both cell lines.

The ELISA analysis showed an IL-6 concentration in the supernatants of the U937 cells of more than 200 µg/ml for both time points in the treated wells and a concentration of 24-34 ng/ml in the untreated wells.

The ELISA analysis showed a CRP concentration of 0.416 pg/ml at 6 h and 0.295 pg/ml at 20 hours. This value was slightly higher than the lower sensitivity limit of the ELISA kit. The concentration of hepcidin was not detected by the ELISA kit at 20 ng/ml. The LPS concentration to be used with this cell line should be greater than 20 ng/ml (40 ng/ml).

4.3 Dilution and Test with Iron Compositions

Before the cells were treated with the selected compounds, they were tested to assess their dissolution properties. The compounds were diluted in sterile PBS and in the standard cell culture medium (EMEM). All of the compounds seemed to be viscous; the iron sulphate was separated in two phases and needed to be vigorously mixed again in order to be resuspended.

An initial ten-fold dilution of all compounds was performed (3 mg/ml of iron): the solutions were rather viscous and the iron sulphate and the pyrophosphate changed the colour (pH) of the medium from red to yellow. The matrix and the vitamin D showed no problems.

A further ten-fold dilution was performed (300 micrograms/ml of iron): the solutions seemed to be less viscous and there was no evident colour change in the medium with iron pyrophosphate; iron sulphate showed a moderate colour change in the medium.

At the dilution used for the experiments (300 times the dilution, 50 g/ml of iron) the compounds were completely dissolved both in PBS and in the medium without emissions of viscosity or changes in colour (pH).

The compounds were tested on U937 and HepG2 cell cultures for 24 hours at a concentration of 50 micrograms/ml of iron. The first test showed a contamination in the cell culture media in all the treated wells, in terms of black patches moving in the culture media. After UV irradiation of the compounds, a second test was performed and revealed no signs of contamination.

At 50 micrograms/ml, the compounds demonstrated to have an effect on the cytoplasmic volume of the cells (loss of volume), in particular the iron sulphate in the U937 cells. Moreover, the compounds had an effect on cell adhesion in the U937 cells. This effect was less evident on the HepG2 cells. However, the quality and quantity of cells in the wells at the end of the treatment were acceptable compared to the untreated wells.

5 Results of Marker Identification.

5.1 Levels of IL-6 in the Supernatants of U937

Figure 1:
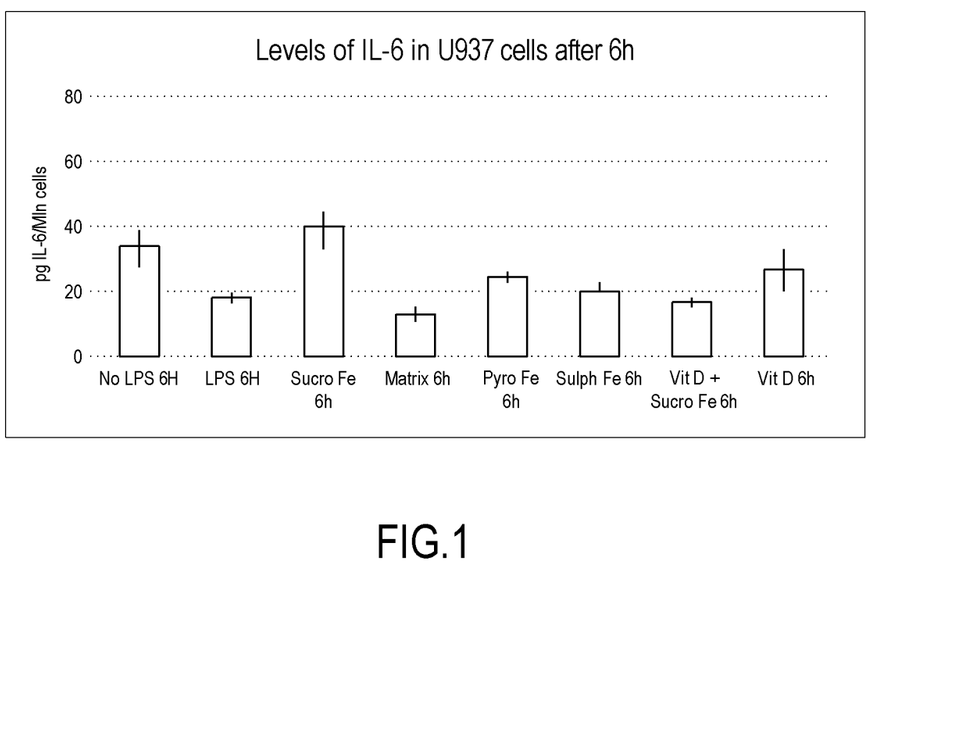

The levels of IL-6 in the supernatants were measured using the ELISA technique. The measurement was performed at 6 hours. The IL-6 levels in the U937 cells at 6 h are summarised in FIG. 1, where one notes a decrease in the IL-6 level in cells treated with the combination of vitamin D+sucrosomial iron (according to the invention) compared to those treated with vitamin D alone or with sucrosomial iron alone.

5.2 Expression of Hepcidin in Supernatants of HepG2 Cells.

Figure 2:
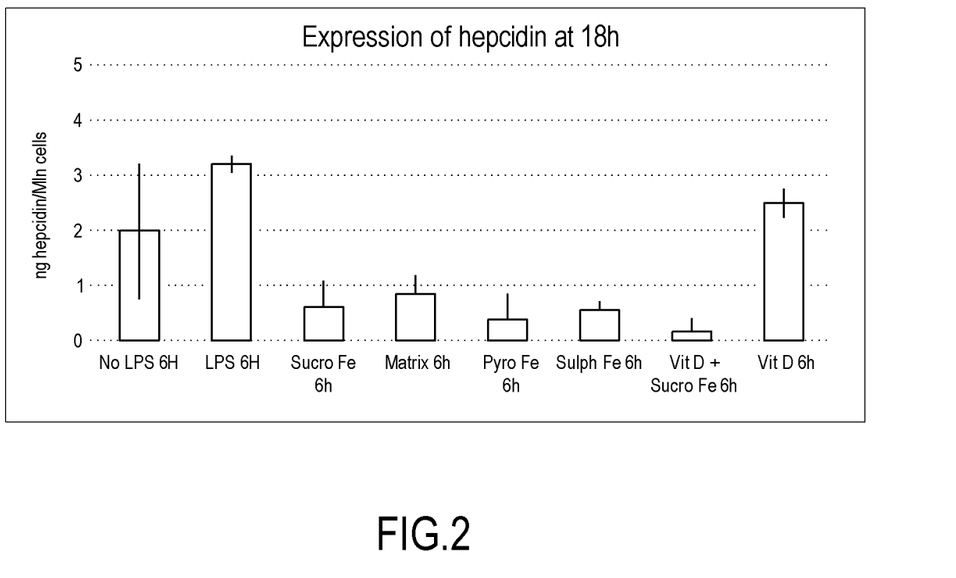

The expression of hepcidin produced by HepG2 cells is shown in FIG. 2. After 18 hours of treatment, the hepcidin levels were higher in the case of treatment with LPD and vitamin D. The cells treated with a combination of vitamin D+sucrosomial iron (according to the invention) showed a lower expression of hepcidin compared to those treated with vitamin D alone or with sucrosomial iron alone.

5.3 Levels of CRP in Supernatants of HepG2

Figure 3:
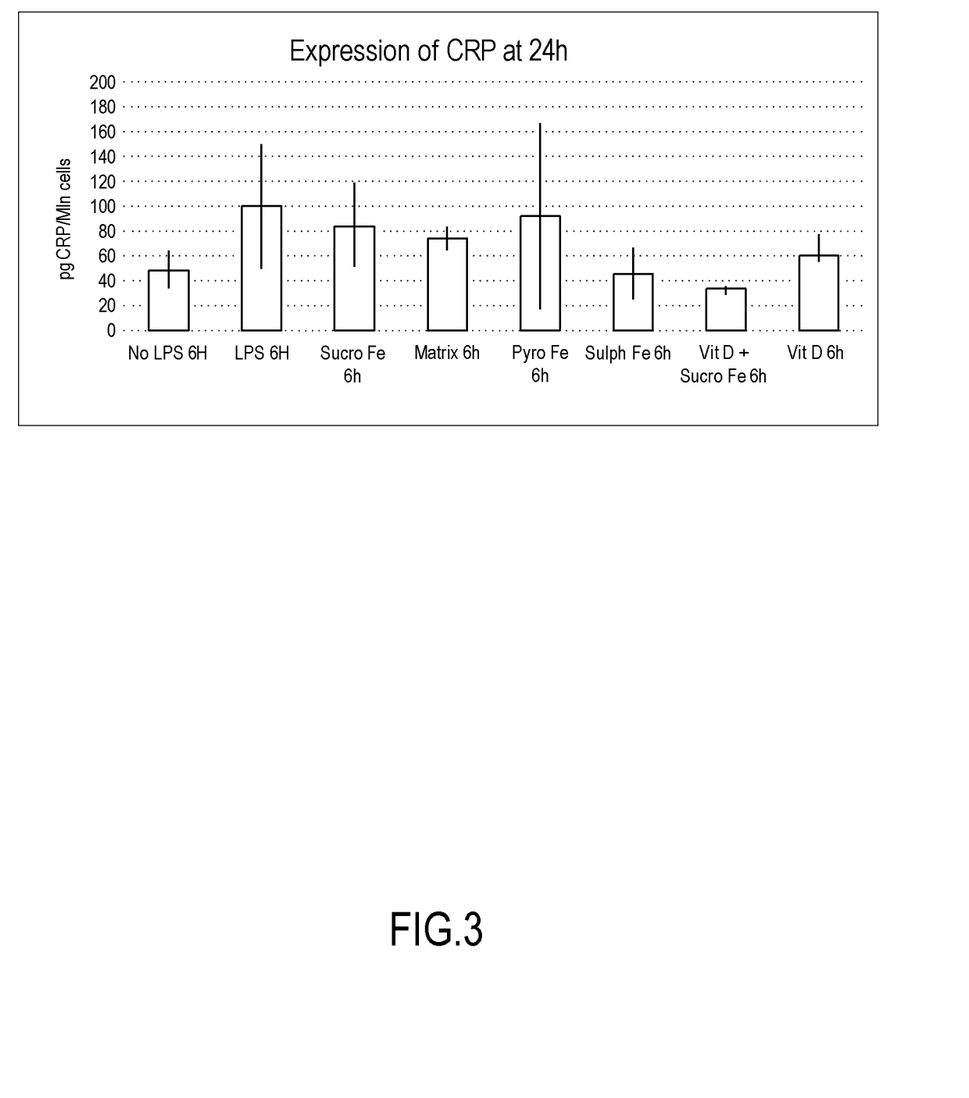
FIG. 3 shows the level of CRP produced by HepG2 cells in the supernatants of cells after 24 hours of treatment with the iron compounds. The type of treatment, analogously to the previous figures, is shown on the x axis. The quantity, in pg/ml, of CRP produced per million cells is represented on the y axis. These results represent a mean of two different experiments.

FIG. 3 shows the levels of CRP (C-reactive Protein) produced by HepG2 cells in supernatants of cells after 24 hours of treatment with iron compounds, vitamin D and the association thereof. The association of vitamin D and sucrosomial iron (according to the present invention) is capable of decreasing CRP expression in a more marked manner than treatments with sucrosomial iron alone and vitamin D alone.

5.4 Conclusions

The combination of vitamin D and an iron oxide, complex or salt according to the present invention produces a marked reduction in the inflammatory markers IL-10, hepcidin and CRP. These results indicate the presence of a synergistic anti-inflammatory effect between component (a), i.e. vitamin D, and component (b), i.e. iron compound, according to the present invention.

II) Clinical Study

AIM

The aim of this study was to assess the support of vitamin D in improving the absorption of iron in patients with sideropenic anaemia and a vitamin D deficiency.

Vitamin D has an anti-inflammatory effect which induces the response of Th2 and Tregs and the polarization of M2 macrophages and production of hepcidin.

Patients and Methods

In group A, 20 patients (M/F: ½), mean age 55 years (R50-70), with vitamin D<10 ng/ml and a median value of haemoglobin (Hb) of 8.5 g/dl (R8-9.5) and a median ferritin value of 20 ng/ml (2-28), were supported with sucrosomial iron 30 mg tid (ter in die, three times a day) for 3 months and cholecalciferol (vitamin D3) 4000 IU/day (according to the invention). In group A the median C-reactive protein (CRP) was 35 ng/ml (R20-47) and 6 patients had a documented bacterial infection.

In group B, 20 patients (M/F: ½), mean age 60 years (R55-68), with vitamin D<10 ng/ml and a median value of Hb of 8.2 g/dl (R8-10) and a median ferritin value of 18 ng/ml (10-30), were supported with sucrosomial iron 30 mg tid for 3 months. In group B the median CRP was 28 ng/ml (R20-32) and 7 patients had a documented bacterial infection.

Results

In group A after 3 months the patients reached a median haemoglobin level of 12.5 g/dl (R 10-13). The patients with a bacterial infection reached a median haemoglobin level of 10 g/dl (R 9-11).

In group B after 3 months the patients reached a median haemoglobin level of 11.5 g/dl (R 9.5-12). The patients with a bacterial infection reached a median Hb level of 9.5 g/dl (R 9-10,5).

CONCLUSION

The administration of vitamin D jointly with the administration of sucrosomial iron (according to the invention) improves iron absorption in patients with a vitamin D deficiency, except in patients with a bacterial infection.

The invention claimed is:

1. A method for the treatment of a pathology or disorder connected to iron deficiency, the method comprising
    administering to a subject in need thereof, an effective amount of a composition comprising
        (a) 4000 IU of a group D vitamin, esters, acetates, or amides thereof, or mixtures thereof,
        (b) a sucrosomial iron in which an iron (III) coordination complex, an iron (III) oxide or an iron (III) salt, formulated in association with a sucrose fatty acid ester in an amount from 10% to 20% by weight and a lecithin in an amount from 0.1% to 1.5% by weight based on the total weight of the composition; and
    optionally, pharmaceutical or food grade excipients, additives or co-formulants, or combinations thereof;
    wherein in said iron (III) coordination complex, one or more atoms, ions or molecules surround the iron (III) at least partially without forming either an ionic or covalent bond; and
    wherein said pathology or disorder connected to iron deficiency is an anaemia of inflammation.

2. The method of claim 1, wherein the composition is formulated for oral administration.

3. The method of claim 1, wherein the sucrosomial iron, is further formulated with a gelatinized or pregelatinized vegetable starch.

4. The method of claim 1, wherein said group D vitamin is vitamin D3 or cholecalciferol.

5. The method of claim 1, wherein said iron (III) salt is iron (III) pyrophosphate.

6. The method of claim 5, wherein the iron (III) pyrophosphate is formulated in association with sucrose fatty acid esters E473, lecithin E322 and, optionally, pregelatinized starch.

7. The method of claim 1, wherein said sucrosomial iron is in an amount from 12.5 to 18.5% by weight based on the total weight of the composition.

8. The method of claim 1, wherein said sucrosomial iron is in an amount from 16 to 18.0% % by weight based on the total weight of the composition.

9. The method of claim 1, wherein the lecithin is in an amount from 0.4 to 1.0% by weight based on the total weight of the composition.

10. The method of claim 1, wherein the lecithin is in an amount from 0.50 to 0.8% by weight % based on the total weight of the composition.

11. The method of claim 3, wherein said gelatinized or pregelatinized vegetable starch is in an amount from 15 to 40%, relative to the weight of the sucrosomial iron.

12. The method of claim 3, wherein said gelatinized or pregelatinized vegetable starch is in an amount from 20 to 35%, relative to the weight of the sucrosomial iron.

13. The method of claim 3, wherein said gelatinized or pregelatinized vegetable starch is in an amount from 25 to 30%, relative to the weight of the sucrosomial iron.

14. A method for the treatment of a pathology or disorder connected to iron deficiency, the method comprising
    administering to a subject in need thereof, an effective amount of a composition comprising:
        (a) 4000 IU of a group D vitamin, esters, acetates, or amides thereof, or mixtures thereof,
        (b) a sucrosomial iron in which iron (III) pyrophosphate is formulated in association with a sucrose fatty acid ester in an amount from 10% to 20% by weight and a lecithin in an amount from 0.1% to 1.5% by weight based on the total weight of the composition; and
    optionally, pharmaceutical or food grade excipients, additives or co-formulants, or combinations thereof;
    wherein said pathology or disorder connected to iron deficiency is an anaemia of inflammation.

15. The method of claim 14, wherein the iron (III) pyrophosphate is formulated in association with sucrose fatty acid esters E473, lecithin E322 and, optionally, pregelatinized starch.

16. The method of claim 14, wherein said group D vitamin is vitamin D3 or cholecalciferol.

17. The method of claim 14, wherein the sucrosomial iron is further formulated with a gelatinized or pregelatinized vegetable starch.

* * * * *